(12) United States Patent
Boehm et al.

(10) Patent No.: US 9,644,076 B2
(45) Date of Patent: May 9, 2017

(54) CROSS-LINKERS FOR HYDROGELS, HYDROGELS INCLUDING THESE CROSS-LINKERS AND APPLICATIONS THEREOF

(71) Applicant: MAX-PLANCK-GESELLSCHAFT ZUR FÖRDERUNG DER WISSENSCHAFTEN E.V., München (DE)

(72) Inventors: Heike Boehm, Weinheim (DE); Valentin Hagel, Springe (DE); Tabea Mundinger, Stuttgart (DE); Isabell Nuss, Munich (DE); Seraphine Valeska Wegner, Heidelberg (DE); Sabine Laschat, Boeblingen (DE); Markus Manfred Mateescu, Constance (DE)

(73) Assignee: Max-Planck-Gesellschaft zur Foerderung der Wissenschafen e. V., Munich (DE)

( * ) Notice: Subject to any disclaimer, the term of this patent is extended or adjusted under 35 U.S.C. 154(b) by 0 days.

(21) Appl. No.: 14/431,300

(22) PCT Filed: Sep. 25, 2013

(86) PCT No.: PCT/EP2013/002876
§ 371 (c)(1),
(2) Date: Mar. 25, 2015

(87) PCT Pub. No.: WO2014/048564
PCT Pub. Date: Apr. 3, 2014

(65) Prior Publication Data
US 2015/0240037 A1 Aug. 27, 2015

(30) Foreign Application Priority Data
Sep. 25, 2012 (WO) .................. PCT/EP2012/004014

(51) Int. Cl.
*C08J 3/24* (2006.01)
*C07D 213/80* (2006.01)
(Continued)

(52) U.S. Cl.
CPC .............. *C08J 3/24* (2013.01); *C07D 213/80* (2013.01); *C07D 213/82* (2013.01);
(Continued)

(58) Field of Classification Search
CPC ................ C07D 213/80; C07D 213/82; C08B 37/0072; C08J 3/075; C08J 2305/08; C08J 3/24; C08L 5/08
(Continued)

(56) References Cited

U.S. PATENT DOCUMENTS

| 4,988,384 A | 1/1991 | Sing et al. |
| 5,439,950 A | 8/1995 | Liao et al. |

(Continued)

FOREIGN PATENT DOCUMENTS

| DE | 2107407 A1 | 12/1971 |
| DE | 2153513 A1 | 5/1973 |

(Continued)

OTHER PUBLICATIONS

Kloxin; Science 2009, 324, 59-63.*
(Continued)

*Primary Examiner* — Noble Jarrell
*Assistant Examiner* — Daniel Carcanague
(74) *Attorney, Agent, or Firm* — Caesar Rivise, PC

(57) ABSTRACT

The present invention relates to novel cross-linkers for hydrogels, in particular for hyaluronan hydrogels, corresponding hydrogels including said cross-linkers and various applications thereof. The cross linker of the invention is a bi- or multifunctional cross-linker comprising or consisting of an aromatic or heteroaromatic ring system with 3-6 C atoms which is coupled via functional groups on at least 2 ring positions with at least 2 terminal groups capable to form a
(Continued)

covalent bond with thiol or amino groups, in particular with thiol groups in a thiol-en reaction. The cross-linker may be charged or uncharged. In a specific embodiment, the terminal groups are coupled to carboxy groups of the aromatic or heteroaromatic ring system via an ester or amide bond. More specifically, the cross-linker of the invention is a derivative of pyridine-3,5-dicarboxylic acid or a corresponding pyridinium salt thereof wherein 2 terminal groups are coupled to the carboxy groups of the pyridine or pyridinium core via an ester or amide bond. In a preferred embodiment, the cross-linker if $N^3,N^5$-bis(2-acrylamidoethyl) pyridine-3,5-dicarboxamide or a 3,5-bis((2-acryl-amidoethyl) carbamoyl)-1-methylpyridin-1-ium-halogenide.

9 Claims, 5 Drawing Sheets

(51) Int. Cl.
| | | |
|---|---|---|
| *C08J 3/075* | (2006.01) | |
| *C07D 213/82* | (2006.01) | |
| *C08B 37/08* | (2006.01) | |
| *C08L 5/08* | (2006.01) | |

(52) U.S. Cl.
CPC .......... *C08B 37/0072* (2013.01); *C08J 3/075* (2013.01); *C08L 5/08* (2013.01); *C08J 2305/08* (2013.01)

(58) Field of Classification Search
USPC ......................................... 514/777
See application file for complete search history.

(56) References Cited

U.S. PATENT DOCUMENTS

| | | | |
|---|---|---|---|
| 2003/0199654 A1 | 10/2003 | Zhang et al. | |
| 2007/0197682 A1 | 8/2007 | Jia et al. | |
| 2010/0032621 A1 | 2/2010 | Itano et al. | |
| 2011/0280914 A1* | 11/2011 | Prestwich | A61L 27/38 424/400 |

FOREIGN PATENT DOCUMENTS

| | | | |
|---|---|---|---|
| JP | 2007025238 A | | 2/2007 |
| WO | WO03072155 | * | 9/2003 |
| WO | 2005103016 A1 | | 11/2005 |
| WO | 2006082412 A2 | | 8/2006 |
| WO | 2011057219 A2 | | 5/2011 |
| WO | 2012157568 A1 | | 11/2012 |

OTHER PUBLICATIONS

Levesque; Bioconjugate Chem. 2007, 18, 874-885.*
Piluso; Int. J. Artif. Organs 2011, 34, 192-197.*
Mohamed; Int. J. Mol. Sci. 2012, 13, 11194-11209.*
Fiore; Biomacromolecules 2009, 10, 128-133.*
Kumar; International Journal of Biological Macromolecules 2009, 45, 330-337.*
Vetrik; Polymer Degradation and Stability 2011, 96, 892-897.*
Joester; J. Am. Chem. Soc., 2006, 128,1119-1124.*
Kurisawa; J. Mater. Chem., 2010, 20, 5371-5375.*
Seliktar; Science 2012, 336, 1124-1128.*
Jin; Journal of Controlled Release 2010,148, e41-e43.*
Muzzarelli; Carbohydrate Polymers 2009, 77, 1-9.*
Cai et al., "Injectable glycosaminoglycan hydrogels for controlled release of human basic fibroblast growth factor", Biomaterials, vol. 26, pp. 6054-6067 (2005).
Chuchuryukin et al., "General approach for template-directed synthesis of macroheterocycles by ring-closing metathesis (RCM)," Adv. Synth. Catal., vol. 347, pp. 447-462 (2005).
Database Reaxys, Database accession Nos. 265191, 3774093 (RIDs) (1956).
Hagel et al., "Desmosine-inspired cross-linkers for hyaluronan hydrogels", Sci. Rep., vol. 3, pp. 1-5 (2013).
Hobson et al., "Poly(amidoamine) hyperbranched systems: synthesis, structure and characterization", Polymer, vol. 40, pp. 1279-1297 (1999).
Kluger et al., "Electrospun poly(D/L-lactide-CO-L-lactide) hybrid matrix: a novel scaffold material for soft tissue engineering", J Mater Sci Mater Med, vol. 21, pp. 2665-2671 (2010).
Kohman et al., "Tuning hydrogel properties and function using substituent effects", Soft Matter, vol. 6, pp. 2150-2152 (2010).
Mohamed et al., "Synthesis and antimicrobial activity of some novel terephthaloyl thiourea cross-linked carboxymethyl chitosan hydrogels", vol. 19, pp. 1879-1891 (2012).
Sambrook et al., "Anion-templated assembly of a [2]catenane", J. Am. Chem. Soc., 126, pp. 15364-15365 and supplemental pp. S1-S5 (2004).
Sheibani et al., "Conformationally restricted dynamic supramolecular catalysts for substrate-selective epoxidations", Org. Biomol. Chem., vol. 10, pp. 2059-2067 (2012).
Shi et al., "Synthesis and crystal structure of metal-organic frameworks [Ln 2 (pydc-3,5)3 (H2O)9]n 3nH2O (Ln= Sm, Eu, Gd, Dy; pydc-3, 5= pyridine-3, 5-dicarboxylate) along with the photoluminescent property of its europium one." J. Mol. Struct., vol. 837, pp. 185-189 (2007).
Shu et al., "Disulfide cross-linked hyaluronan hydrogels", Biomacromolecules, vol. 3, pp. 1304-1311 (2002).
Southan et al., "Toward controlling the formation, degradation behavior, and properties of hydrogels synthesized by aza-Michael reactions", Macromol. Chem. Phys., vol. 214, pp. 1865-1873 (2013).
Van Vlierberghe et al., "Biopolymer-based hydrogels as scaffolds for tissue engineering applications: A review", Biomacromolecules, vol. 12, pp. 1387-1408 (2011).
International Search Report for PCT/EP2013/002876 dated Nov. 12, 2013.
English-language abstract for JP2007025238 (2007).

* cited by examiner

CROSS-LINKERS FOR HYDROGELS, HYDROGELS INCLUDING THESE CROSS-LINKERS AND APPLICATIONS THEREOF

BACKGROUND OF THE INVENTION

The present invention relates to novel cross-linkers for hydrogels, in particular for hyaluronan hydrogels, corresponding hydrogels including said cross-linkers and various applications thereof.

The future challenges of an aging society and associated health problems such as the increasing need for regenerative medical devices have stimulated worldwide research efforts in the field of tissue engineering. Particular attention has been focused on hydrogels including those made from polymers such as polyethylene glycol diacrylates (PEG-DA), polyglycerol diacrylates and chemically modified hyaluronic acid (HA) such as thiolated HA (HA-SH), exploiting their hydrophilicity as well as high biocompatibility.

Hyaluronic acid is an evolutionary well-preserved linear, polycationic sugar found in all connective tissues that can promote elastin formation in tissue culture. HA-based hydrogels have been studied extensively and are used in a wide variety of applications such as for medical implants, tissue engineering, cell culture and drug delivery.

However, hyaluronic acid is not a bio-inactive material. For example, HA and its derivatives can be degraded by hyaluronidases to short fragments, causing undesirable side reactions. Moreover, many cells having specific membrane receptors, such as CD44, LYVE1 or RHAMM, can bind to HA and interact therewith.

In view of these shortcomings of HA hydrogels of the prior art, an object of the present invention is to provide improved HA hydrogels which maintain the advantages of the known HA gels but which are bio-inactive or whose bioactivity is adjustable on demand.

A further related object of the invention is to provide means for preparing such hydrogels.

These objects are achieved by providing the cross-linker and the hydrogel of the invention.

DESCRIPTION OF THE INVENTION

The cross linker of the invention is a bi- or multifunctional cross-linker comprising or consisting of an aromatic or heteroaromatic ring system with 3-6 C atoms which is coupled via functional groups on at least 2 ring positions with at least 2 terminal groups capable to form a covalent bond with thiol or amino groups, in particular with thiol groups in a thiol-en reaction.

In a preferred embodiment, the cross-linker comprises a heteroaromatic ring system with at least one heteroatom. Said heteroatom(s) is/are selected from the group consisting of N, S, Se, O.

The heteroaromatic ring system may for example be selected from the group comprising pyrroles, pyridines, pyrimidines, pyrazoles, imidazoles, furans, dioxins, oxazoles, thiophenes, thiazoles, thiazines.

In specific embodiments of the invention, the aromatic or heteroaromatic ring system of the cross-linker bears a negative or positive charge or no charge.

The charge may be provided by a charged heteroatom of a heteroaromatic ring system as defined above or, alternatively, the charge may be provided by charged side chain of an aromatic or heteroaromatic ring system. This side chain may be specifically cleavable under predetermined conditions.

In a specific embodiment, the terminal groups are selected from the group consisting of acrylates and acrylamides.

The terminal groups may be coupled to the aromatic or heteroaromatic ring system via functional groups of said aromatic or heteroaromatic ring system at any position which does not impair the desired properties of the cross-linker.

Principally, the functional groups may be any group capable to form a covalent bond with a corresponding reactive group. Some non-limiting examples are alcohol, amine or carboxy groups.

In a specific embodiment, the terminal groups are coupled to carboxy groups of the aromatic or heteroaromatic ring system via an ester or amide bond. Amide bonds are preferred.

More specifically, the cross-linker of the invention is a derivative of pyridine-3,5-dicarboxylic acid or a corresponding pyridinium salt thereof wherein 2 terminal groups are coupled to the carboxy groups of the pyridine or pyridinium core via an ester or amide bond. Amide bonds generally result in more stable gels and, thus, are preferred.

In an especially preferred embodiment, the cross-linker is $N^3,N^5$-bis(2-acrylamidoethyl)pyridine-3,5-dicarboxamide or a 3,5-bis((2-acrylamidoethyl)carbamoyl)-1-methylpyridin-1-ium-halogenide.

Principally, the cross-linkers of the present invention are suited for cross-linking a broad range of polymers or biopolymers, in particular thiolated or aminated (bio)-polymers. The cross-linkers of the present invention are particularly suited for cross-linking thiolated or aminated polysaccharide-based biopolymers such as hyaluronic acid etc.

The use of these cross-linkers enables to impart favourable properties to the resulting cross-linked hydrogels. For example, their use enables to provide hydrogels which are bio-inactive or whose bioactivity is adjustable on demand.

Consequently, a further aspect of the invention relates to hydrogels which are cross-linked with a bi- or multifunctional linker as defined above.

More specifically, these hydrogels are obtained by cross-linking thiolated or aminated (bio)polymers with a bi- or multifunctional linker as defined above. In particular, the (bio)polymer may be selected from the group comprising polysaccharides and polyaminosaccharides, such as cellulose, chitin, chitosan, chondroitinsulfate, dextran, hyaluronic acid and block-copolymers and derivatives thereof, alginates, poly(lactic) acid, PEG, as well as block-copolymers and derivatives of any of these polymers. The basic polymers may be derivatized by methods known in the art. In particular, thiol groups, amino groups or other desired functional groups can be introduced by methods known in the art. Further suitable basic polymers and derivatives thereof are disclosed by Van Vlierberghe et al. in *Biomacromolecules* 2011, 1387-1408.

In an especially preferred embodiment, the hydrogel comprises at least partially thiolated hyaluronic acid.

By varying the degree of thiolation and/or the ratio of cross-linker:thiol groups, the swelling behaviour as well as the mechanical properties of the hydrogels can be adjusted (as demonstrated by FIG. 1A-1C). The HA hydrogels of the invention presented in FIG. 1 show a linear elastic behaviour up to 20% compression and are extremely formstable under repetitive compression up to 60%.

Typically, the degree of thiolation of the hyaluronic acid used for the preparation of hydrogels according to the invention is in the range of from 25%-90%, such as 30%-80%, preferably 40%-70%.

As already indicated above, by selecting an appropriate cross-linker it is possible to adjust the bioactivity and stability of a hydrogel according to the invention. For example, HA hydrogels prepared by using HA having a degree of thiolation below 50% and the positively charged cross-linker 5b are not degraded by hyaluronidase (FIG. 2B) and REF 52WT cells are not able to adhere thereto. In contrast to this, HA hydrogels prepared by using HA having the same degree of thiolation and the neutral cross-linker 5a are degraded by hyaluronidase within a few hours (FIG. 2A) and REF 52WT cells adhere thereto and can be cultivated on these gels.

HA hydrogels prepared by using HA having a degree of thiolation above 50% (e.g. 58%) and cross-linked by either the neutral cross-linker 5a or the positively charged cross-linker 5b are not degraded by hyaluronidase (FIG. 3A-3B). However, they differ with respect to their adhesion characteristics. REF 52WT cells adhere to the gels with the neutral cross-linker 5a but not (or much less) to the gels with the charged cross-linker 5b (FIG. 4A-4D).

In a specific embodiment of the invention, the charge of at least one cross-linker is adjustable in response to the pH of the hydrogel's surrounding. Thus, the bioactivity of such a hydrogel is also adjustable by the pH.

In a specific embodiment, the hydrogel is cross-linked with a combination of at least 2 different cross-linkers. This enables a further favourable adjustment of the corresponding gel's properties on demand.

For example, in the application wherein the hydrogel is used for a tissue graft, the second cross-linker may be slowly degradable in the target tissue, thus, after a certain period of time the properties of the gel will be determined only be by the first cross-linker. This enables, e.g., to change the adhesion (or other) properties of the gel in a time-dependent manner.

At least one cross-linker may also bear further functional groups of interest, such as adhesion peptides, growth factors, a specifically degradable sequence (which may be charged), drugs etc.

In another specific embodiment, the hydrogel of the invention may comprise different layers with different characteristics. For example, the top layer may be cell-adhesive (e.g. for endothelial cells), whereas the bottom layer may be anti-adhesive and thus preventing the adhesion of undesired cells and deposition of debris.

The hydrogels according to the invention may be decorated with covalent bound nanoparticles, in particular gold nanoparticles, by means of transfer nanolithography as principally disclosed in e.g. EP 05 782 590.3. These nanoparticles may also be functionalized by functional groups of interest, such as adhesion peptides and other (bio)active substances.

The resulting soft, linear elastic and bioactive hydrogels which are preferably functionalized in a specific manner represent a novel well-defined cell culture system for investigating the behaviour of cells as a function of the mechanical properties of their surroundings. Hitherto, such investigations could only be implemented with the linear elastic but considerably more rigid polyacrylamide or the soft PEG hydrogels which, however, show linear elasticity only over a very narrow range.

The hydrogels may be present on a 2- or 3-dimensionally extended surface or as gel particles. In a specific embodiment, said 2- or 3-dimensional surface or gel particles may be present in a fluid medium, e.g. a fluid medium containing a cell suspension.

The present invention also relates to a material composition comprising a hydrogel as defined above and optionally further components, such as fillers, reinforcing materials, carrier systems, matrices etc., and/or (bio)active substances such as antibodies, enzymes, drugs, growth factors etc.

In particular for drug delivery, the gels may by used as an passive biocompatible material for coating nano- or microcompartments with active substances or as a matrix for active substances directly incorporated into the gel. The release of active substances may be controlled by means of a degradable and/or pH-sensitive cross-linker. The active substance may be also an aqueous medium (e.g. for use in a cosmetic anti-wrinkle composition).

In view of their favourable properties, the hydrogels according to the invention or the material composition comprising the same are very useful for a broad range of applications, in particular in the fields of surface chemistry, biology, biochemistry, medicine and cosmetics, in particular in the fields of tissue engineering, implantology, cell culture applications and drug delivery.

More specifically, they are suitable for use as carrier systems, matrices and substrates for cells, tissues and (bio) active materials, including enzymes, antibodies, drugs etc. in applications such as intra-ocular stents and many others.

These applications represent a further aspect of the present invention.

The following description focuses on the synthesis of cross-linkers derived from pyridine-3,5-dicarboxylic acid and the corresponding HA hydrogels. However, the skilled artisan will recognize that analogous reactions can be performed with other aromatic or heteroaromatic ring systems as well and will lead to compounds with similar properties, in particular the capability to act as cross-linkers for hydrogels, in particular thiolated HA-based hydrogels, but other hydrogels a well.

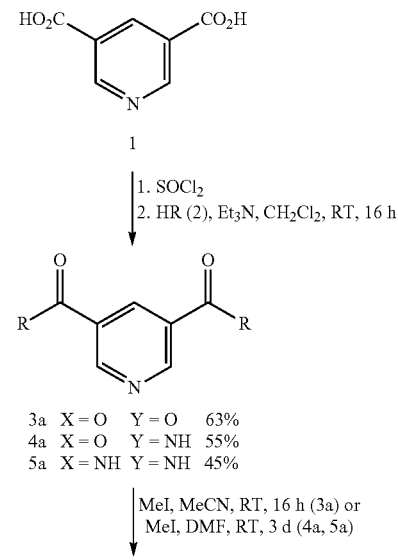

Scheme 1. Synthesis of selected pyridine-based cross-linkers

-continued

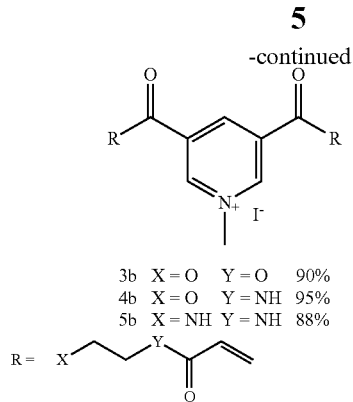

| | X | Y | |
|---|---|---|---|
| 3b | O | O | 90% |
| 4b | O | NH | 95% |
| 5b | NH | NH | 88% |

The synthesis commenced with conversion of pyridine-3,5-dicarboxylic acid 1 (Scheme 1) to the corresponding acid chloride followed by condensation with the acrylate units 2 according to a modified procedure by van Koten et al. (A. V. Chuchurykin, P. A. Chase, H. P. Dijkstra, B. M. J. M. Suijerbuijk, A. M. Mills, A. L. Spek, G. P. M. van Klink, G. van Koten, Adv. Synth. Catal. 2005, 347, 447-462) and gave the pyridines 3a-5a in 45%-63% yield. Subsequent N-methylation provided the N-methylpyridinium salts 3b-5b in 88%-90% yield. The obtained cross-linkers were used for the thiol-Michael reaction with HA-SH in aqueous media to give the corresponding hydrogels.

Initial rheological measurements revealed that HA-hydrogels cross-linked with 5a and 5b are considerably more long-term stable than corresponding gels formed with cross-linkers 3a-4b and, consequently, these gels were employed for subsequent characterization.

BRIEF DESCRIPTION OF THE FIGURES

FIG. 1A shows stress-strain curves for HA-SH-5a (black) and HA-SH-5b (white) hydrogels with 1.0 cross-linker equiv.

FIG. 1B shows E-moduli of HA-SH-5a (black) and HA-SH-5b (white) hydrogels measured by uniaxial compression testing between parallel plates.

FIG. 1C shows the swelling ratio of HA-SH-5a (black) and HA-SH-5b (white) hydrogels.

FIG. 2A: cross-linker 5a
FIG. 2B: cross-linker 5b

FIG. 3A: cross-linker 5a
FIG. 3B: cross-linker 5b

FIG. 4A: cross-linker 5a; after seeding

EXAMPLE 1

Preparation of Cross-Linkers

Materials

Figure 1A:
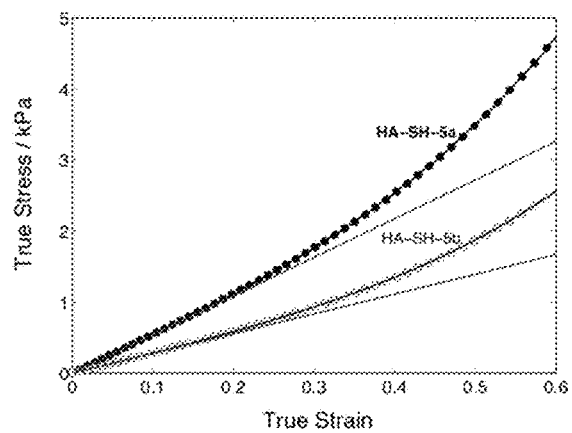
FIGS. 1A, 1B and 1C illustrates relevant mechanical properties of HA-hydrogels cross-linked with 5a and 5b, respectively.

All chemicals for the synthesis of the cross-linkers were purchased from Sigma-Aldrich or Alfa-Aesar. Acryloyl chloride, dichloromethane and triethylamine (dichloromethane and triethylamine were distilled over calcium hydride) were freshly distilled before use.

Synthesis of pyridine-3,5-dicarboxylic acid

Pyridine-3,5-dicarboxylic acid 1 was prepared by oxidation of 3,5-lutidine according to Shi et al., J. Mol. Struct. 2007, 837, 185-189.

Preparation of N-(2-aminoethyl)acrylamide (2: X, Y=NH)

Scheme 2. Synthesis of N-(2-aminoethyl) acrylamide 2

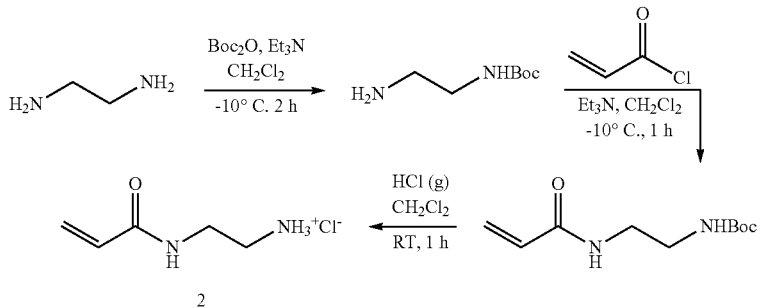

N-(2-aminoethyl)acrylamide 2 was prepared in three steps. The first two steps were carried out according to the literature (L. J. Hobson, W. Feast, Polymer 1999, 40, 1279-1297.). The third step was modified to assure that the amino hydrochloride did not contain any water before use in the following acylation. The protected N-t-Butoxycarbonyl-N'-acryloyl-1,2-diaminoethane (12.8 g, 59.8 mmol) was dissolved in dry dichloromethane (60 mL) and gaseous hydrogen chloride was passed through the solution until the deprotection was complete (usually 1 h at RT, TLC monitoring). During the deprotection, a white precipitate formed.

After completion of the reaction, 4-methoxyphenole (10 mg, 0.081 mmol) was added as polymerization inhibitor and the mixture was concentrated under reduced pressure to remove any byproducts of the deprotection. A colorless solid was obtained (7.98 g, 54 mmol, 89%). Dichloromethane (40 mL) and triethylamine (17.4 mL, 126 mmol) were added to the product as preparation for the following acylation.

$^1$H-NMR (300 MHz, D$_2$O): δ=3.12-3.21 (m, 2H, 2-H$_2$), 3.57-3.61 (m, 2H, 1-H$_2$), 5.80 (dd, J=8.9 Hz, J=2.6 Hz, 1H, CH$_2$=CH), 6.22 (dd, J=17.2 Hz, J=2.6 Hz, 1H, CH$_2$=CH), 6.29 (dd, J=17.2 Hz, J=8.9 Hz, 1H, CH$_2$=CH) ppm. $^{13}$C-NMR (75 MHz, D$_2$O): 6=36.8 (C-1), 39.2 (C-2), 127.5 (CH$_2$=CH), 128.0 (CH=CH$_2$), 169.4 (C=O) ppm. Spectral data according to literature (Hobson, above).

General Procedure for the Preparation of Acryloyl-Pyridines

A typical procedure (modified procedure of Chuchuryukin, van Koten et al., *Adv. Synth. Catal.* 2005, 347, 447-462) for the preparation was as follows: Pyridine-3,5-dicarboxylic acid 1 (5.00 g, 29.9 mmol) and thionyl chloride (40 mL, 552 mmol) were heated under reflux at 100° C. for 3 h. Excess thionyl chloride was completely removed in vacuo and the residue reconcentrated from toluene to remove residual thionyl chloride. The resulting, slightly yellow acid chloride dissolved in anhydrous dichloromethane (40 mL). This solution was added dropwise at 0° C. to a mixture of the corresponding acryloyl alcohol or amine derivative 2 (59.8 mmol) in dichloromethane (40 mL) and triethylamine (8.70 mL, 62.8 mmol). The reaction mixture was stirred for 16 h and then processed further to purify the crude product.

Bis(2-(acryloyloxy)ethyl) pyridine-3,5-dicarboxylate (3a)

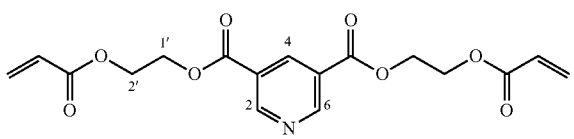 [SMILES: C=CC(=O)OCCOC(=O)c1cncc(C(=O)OCCOC(=O)C=C)c1]

The reaction mixture was filtered (Celite), concentrated to dryness and purified by column chromatography (CH$_2$Cl$_2$/EtOAc/Et$_3$N 5:1:0.005, then 3:1:0.005) to give a clear colorless oil (8.69 g, 23.9 mmol, yield: 63%).

FT-IR (ATR): ν=2957 (w), 2560 (w), 1966 (w), 1720 (s), 1233 (s), 1180 (s), 744 (s) cm$^{-1}$. $^1$H-NMR (300 MHz, CDCl$_3$): δ=4.52-4.56 (m, 4H, 1'-H$_2$), 4.62-4.66 (m, 4H, 2'-H$_2$), 5.88 (dd, J=10.5 Hz, J=1.5 Hz, 2H, CH$_2$=CH), 6.16 (dd, J=17.4 Hz, J=10.5 Hz, 2H, CH=CH$_2$), 6.45 (dd, J=17.4 Hz, J=1.5 Hz, 2H, CH$_2$=CH), 8.87 (t, J=2.1 Hz, 1H, 4-H), 9.38 (d, J=2.1 Hz, 2H, 2-H, 6-H) ppm. $^{13}$C-NMR (75 MHz, CDCl$_3$): δ=62.0 (C-2'), 63.5 (C-1'), 125.8 (C-4), 127.9 (CH=CH$_2$), 131.7 (CH$_2$=CH), 138.3 (C-3, C-5), 154.5 (C-2, C-6), 164.2 (vinyl-C=O), 165.9 (3-C=O, 5-C=O) ppm. MS (ESI): m/z=386.1 [M+Na]$^+$, 364.1 [M+H]$^+$, 270.1. HRMS (ESI): calc. for C$_{17}$H$_{17}$NO$_8$ 386.0846, found 386.0847 [M+Na]$^+$. CHN-Analysis calc.: C 56.33%, H 4.74%, N 3.81%, found: C 56.26%, H 4.81%, N 3.67%.

Bis(2-acrylamidoethyl) pyridine-3,5-dicarboxylate (4a)

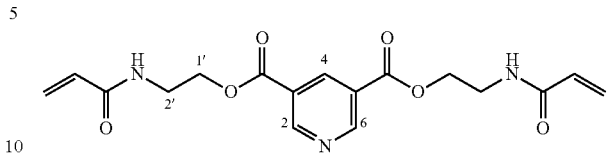

The reaction mixture was filtered (Celite), concentrated to dryness and purified by column chromatography (EtOAc/Acetone/Et$_3$N 10:1:0.005, then 5:1:0.005) to give a colorless solid (7.35 g, 20.3 mmol, yield: 55%), mp=128° C.

FT-IR (ATR): ν=3242 (m), 3070 (m), 1966 (w), 1721 (s), 1553 (s), 1264 (s), 1243 (s), 1115 (m), 752 (m) cm$^{-1}$. $^1$H-NMR (300 MHz, MeOD): δ=3.74 (t, J=5.2 Hz, 4H, 2'-H$_2$), 4.53 (t, J=5.2 Hz, 4H, 1'-H$_2$), 5.07 (bs, 2H, NH), 5.76 (dd, J=9.5 Hz, J=2.3 Hz, 2H, CH$_2$=CH), 6.21 (dd, J=17.2 Hz, J=2.3 Hz, 2H, CH$_2$=CH), 6.30 (dd, J=17.2 Hz, J=9.5 Hz, 2H, CH$_2$=CH), 6.88 (t, J=2.0 Hz, 1H, 4-H), 9.30 (d, J=2.0 Hz, 2H, 2-H, 6-H) ppm. $^{13}$C-NMR (125 MHz, MeOD): δ=39.4 (C-2'), 65.6 (C-1'), 127.1 (CH$_2$=CH), 127.8 (C-3, C-5), 131.9 (CH$_2$=CH), 139.5 (C-4), 154.9 (C-2, C-6), 165.5 (vinyl-C=O), 168.6 (3-C=O, 5-C=O) ppm. MS (EI): m/z=361.0 [M]$^+$, 265.0, 220.0, 150.0, 97.0, 67.0, 55.0 [acryl]$^+$. HRMS (ESI): calc. for C$_{17}$H$_{19}$N$_3$O$_6$ 384.1166, found 384.1170 [M+Na]$^+$. CHN-Analysis calc.: C 56.51%, H 5.30%, N 11.63%, found: C 56.51%, H 5.38%, N 11.59%.

N$^3$,N$^5$-bis(2-acrylamidoethyl)pyridine-3,5-dicarboxamide (5a)

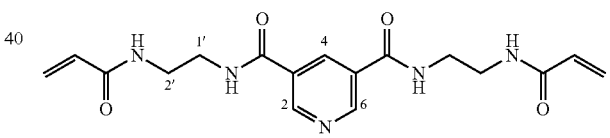

The crude product was washed with dichloromethane to remove triethylammonium chloride until a white powder remained in the filter. The dichloromethane filtrate was concentrated and the obtained solid was suspended in acetone to re-extract product that was solved in dichloromethane. The acetone suspension was filtered and the filtrate concentrated to dryness. The obtained solid was combined with the first washed solid and the total amount recrystallized in methanol to give a colorless solid (4.84 g, 13.5 mmol, yield: 45%), mp=295° C. (decomp.).

FT-IR (ATR): ν=3258 (w), 2945 (w), 1638 (m), 1533 (s), 1236 (m), 671 (m) cm$^{-1}$. $^1$H-NMR (500 MHz, D$_2$O): δ=3.55-3.58 (m, 4H, 2'-H$_2$), 3.62-3.65 (m, 4H, 1'-H$_2$), 5.75 (dd, J=10.1 Hz, J=1.3 Hz, 2H, CH$_2$=CH), 6.16 (dd, J=17.1 Hz, J=1.3 Hz, 2H, CH$_2$=CH), 6.26 (dd, J=17.1 Hz, J=10.1 Hz, 2H, CH=CH$_2$), 9.14 (t, J=1.9 Hz, 1H, 4-H), 9.28 (d, J=1.9 Hz, 2H, 2-H, 6-H) ppm. $^{13}$C-NMR (125 MHz, D$_2$O+TFA): δ=38.4 (C-2'), 39.8 (C-1'), 127.4 (CH=CH$_2$), 129.9 (CH$_2$=CH), 133.5 (C-3, C-5), 142.5 (C-4), 143.3 (C-2, C-6), 163.9 (vinyl-C=O), 170.0 (3-C=O, 5-C=O) ppm. MS (ESI): m/z=382.2 [M+Na]$^+$, 360.2 [M+H]$^+$. HRMS (ESI): calc. for C$_{17}$H$_{21}$N$_5$O$_4$ 382.1486, found 382.1473

[M+Na]⁺. CHN-Analysis calc.: C 56.82%, H 5.89%, N 19.49%, found: C 56.30%, H 5.93%, N 19.33%.

Preparation of N-methyl pyridinium iodides 3,5-bis((2-(acryloyloxy)ethoxy)carbonyl)-1-methyl-pyridin-1-ium iodide (3b)

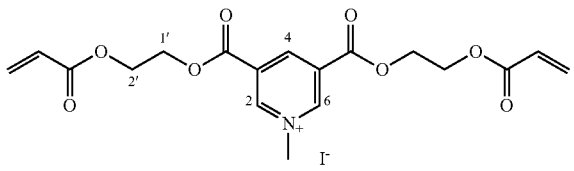 [SMILES: C=CC(=O)OCCOC(=O)c1cc(C(=O)OCCOC(=O)C=C)c[n+](C)c1 ; [I-]]

Bis(2-(acryloyloxy)ethyl) pyridine-3,5-dicarboxylate 3a (500 mg, 1.38 mmol) was treated with methyl iodide (0.43 mL, 6.88 mmol) in acetonitrile (4 mL) for 16 h at room temperature. The solvent was removed in vacuo and the crude product purified by column chromatography (EtOAc/MeCN 1:1) to give a red oil (632 mg, 1.25 mmol, yield: 91%).

FT-IR (ATR): ν=3431 (w), 3005 (w), 2554 (w), 1965 (w), 1715 (s), 1247 (s), 1181 (s), 741 (m) cm⁻¹. ¹H-NMR (300 MHz, CDCl₃): δ=4.56-4.59 (m, 4H, 1'-H₂), 4.70-4.73 (m, 4H, 2'-H₂), 4.86 (s, 3H, N—CH₃), 5.89 (dd, J=10.4 Hz, J=1.4 Hz, 2H, CH₂=CH), 6.16 (dd, J=17.3 Hz, J=10.4 Hz, 2H, CH=CH₂), 6.46 (dd, J=17.3 Hz, J=1.4 Hz, 2H, CH₂=CH), 9.29 (t, J=1.5 Hz, 1H, 4-H), 9.83 (d, J=1.5 Hz, 2H, 2-H, 6-H) ppm. ¹³C-NMR (75 MHz, CDCl₃): δ=51.2 (CH₃), 61.7 (C-2'), 65.2 (C-1'), 127.8 (CH=CH₂), 130.0 (C-3, C-5), 132.1 (CH₂=CH), 145.1 (C-4), 149.8 (C-2, C-6), 160.5 (vinyl-C=O), 166.0 (3-C=O, 5-C=O) ppm. MS (ESI): m/z=378.1 [M-I]⁺. HRMS (ESI): calc. for C₁₈H₂₀INO₈ 378.1183, found 378.1186 [M-I]⁺. CHN-Analysis calc.: C 42.79%, H 3.99%, N 2.77%, I 25.12%, found: C 40.29%, H 4.14%, N 2.56%, I 26.77%.

3,5-bis((2-acrylamidoethoxy)carbonyl)-1-methyl-pyridin-1-ium iodide (4b)

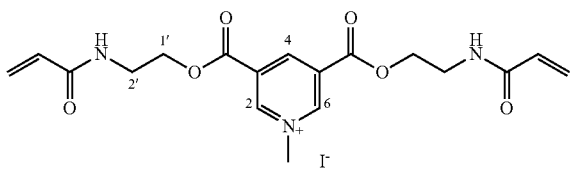 [SMILES: C=CC(=O)NCCOC(=O)c1cc(C(=O)OCCNC(=O)C=C)c[n+](C)c1 ; [I-]]

Bis(2-acrylamidoethyl) pyridine-3,5-dicarboxylate 4a (455 mg, 0.277 mmol) was treated in DMF with methyl iodide (0.39 mL, 6.30 mmol). After 4 d stirring at room temperature the solvent was evaporated completely. The orange residue was dissolved in water (20 mL). and washed with dichloromethane (2×20 mL). The water phase was concentrated to an orange oil. An orange hygroscopic foam was obtained (584 mg, 1.16 mmol, 92%).

FT-IR (ATR): ν=3225 (w), 1649 (s), 1508 (s), 1215 (s), 830 (m), 733 (m) cm⁻¹. ¹H-NMR (300 MHz, D₂O): δ=3.75-3.78 (m, 4H, 2'-H₂), 4.57 (m, 3H, CH₃), 4.60-4.64 (m, 4H, 1'-H₂), 5.78 (dd, J=9.8 Hz, J=1.8 Hz, 2H, CH₂=CH), 6.19 (dd, J=17.1 Hz, J=1.8 Hz, 2H, CH₂=CH), 6.30 (dd, J=17.1 Hz, J=9.8 Hz, 2H, CH=CH₂), 9.43 (dt, J=1.6 Hz, J=0.5 Hz, 1H, 4-H), 9.64 (dd, J=1.6 Hz, J=0.6 Hz, 2H, 2-H, 6-H) ppm. ¹³C-NMR (125 MHz, MeOD): δ=39.2 (C-2'), 50.0 (CH₃), 67.1 (C-1'), 127.3 (CH=CH₂), 131.9 (CH₂=CH), 132.1 (C-3, C-5), 146.1 (C-2, C-6), 151.1 (C-4), 162.2 (vinyl-C=O), 168.6 (3-C=O, 5-C=O) ppm. MS (ESI): m/z=430.2 [M+Na]⁺, 376.2 [M]⁺, 279.1, 182.0. HRMS (ESI): calc. for C₁₈H₂₂IN₃O₆ 376.1487, found. 376.1503 [M]⁺.

3,5-bis((2-acrylamidoethyl)carbamoyl)-1-methyl-pyridin-1-ium iodide (5b)

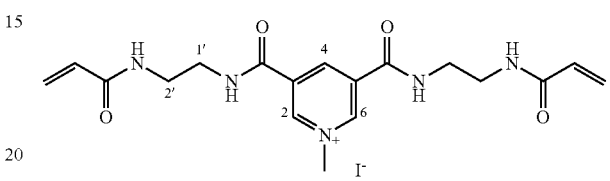

N³,N⁵-bis(2-acrylamidoethyl)pyridine-3,5-dicarboxamide 5a (500 mg, 1.39 mmol) was treated with methyl iodide (0.28 mL, 4.18 mmol) in DMF (30 mL) at room temperature for 3 d. The mixture was evaporated and the residue precipitated and washed with acetonitrile (20 mL) to give a yellow solid. The filtrate from the washing was concentrated to 5 mL and diethyl ether was added. The yellow precipitate that formed was washed again with diethyl ether and combined with the first yellow solid (623 mg, 1.24 mmol, yield: 89%), mp=134° C.

FT-IR (ATR): ν=3356 (w), 3240 (m), 3063 (w), 1654 (s), 1541 (s), 1233 (m), 668 (s) cm⁻¹. ¹H-NMR (300 MHz, D₂O): δ=3.55-3.6 (m, 4H, 2'-H₂), 3.63-3.67 (m, 4H, 1'-H₂), 4.54 (s, 3H, CH₃), 5.77 (dd, J=9.8 Hz, J=1.8 Hz, 2H, CH₂=CH), 6.17 (dd, J=17.2 Hz, J=1.8 Hz, 2H, CH₂=CH), 6.28 (dd, J=17.2 Hz, J=9.8 Hz, CH=CH₂), 9.10 (dt, J=1.7 Hz, J=0.4 Hz, 1H, C-4), 9.36 (dd, J=1.7 Hz, J=0.5 Hz, 2H, C-2, C-6) ppm. ¹³C-NMR (125 MHz, D₂O): δ=41.3 (C-2'), 42.9 (C-1'), 52.0 (CH₃), 130.4 (CH=CH₂), 133.0 (CH₂=CH), 137.4 (C-3, C-5), 144.5 (C-4), 149.7 (C-2, C-6), 166.2 (vinyl-C=O), 172.1 (3-C=O, 5-C=O) ppm. MS (ESI): m/z=374.2 [M-I]⁺. HRMS (ESI): calc. for C₁₈H₂₄IN₅O₄ 374.1823, found 374.1829 [M-I]⁺. CHN-Analysis calc.: C 43.12%, H 4.83%, N 13.97%, found: C 41.72%, H 4.80%, N 13.36%.

EXAMPLE 2

Preparation and Characterization of Hydrogels

HA Hydrogel Formation

The thiolated hyaluronan (HA-SH) was synthesized as described in the literature (X. Z. Shu et al. in *Biomacromolecules* 2002, 3, 1304-1311) with high molecular weight hyaluronan (Sigma-Aldrich) leading to HA-SH molecules with an average of 450 kDa. The number of thiol groups in HA-SH was quantified using the Ellman's assay. HA-SH was dissolved in PBS (Gibco) at 4 mg/ml and the pH was adjusted to 9.0. The cross-linkers were dissolved in a 50/50 (v/v) mixture PBS/ethanol at appropriate concentrations. All solutions used were degassed by sonication for 15 min to avoid oxidation reactions such as the formation of disulfide bonds.

For mechanical testing cylindrical hydrogels were formed. 70 µl of HA-SH (49% thiolation) solution was mixed with 30 µl of cross-linker solution giving a final HA-SH concentration of 2.8% in the gel. The mixture of the precursor solutions was gently vortexed for 3 s to obtain a homogeneous mixture. Thereafter the solution was immediately filled in cylindrical wells (r=3 mm, h=3 mm), closed with a glass slide and the mixture was left to gel for 24 h at 37° C. The hydrogels were then swollen to equilibrium for 48 h in PBS.

For the cell adhesion tests hydrogels (degree of thiolation 58%) were prepared in disk-shaped teflon forms (r=11 mm; h=1.5 mm) using the same method of preparation.

Rheological Measurements During Gel Formation

The rheological properties as the hyaluronan hydrogels formed were measured on a Kinexus Rheometer (Malvern) using a parallel plate geometry. In a typical experiment, 80 µl of polymerization mixture (40% thiolated HA-SH) was placed between the plates, at a distance set to 0.2 mm. The frequency of oscillation was set to 1 Hz and the amplitude to 1%. During the polymerization, the changes in elastic and viscous moduli and of the phase angle were monitored. Before starting the measurement the solvent trap of the rheometer was flooded with Ar using a rebound valve attached to the trap in order to avoid oxidation side reactions. Also before starting the measurements PBS was used to close the air gaps of the solvent trap so that the inside of the trap was hermetically sealed. Furthermore PBS was filled in a ring cavity within the solvent trap to prevent drying-out during the gel formation.

Initial rheological measurements revealed that HA-hydrogels cross-linked with 5a and 5b are considerably more long-term stable than corresponding gels formed with cross-linkers 3a-4b and, consequently, these gels were employed for subsequent characterization.

Ellman's Assay with Hydrogels

40 µl of the gelation mixture was prepared in eppendorf tubes (2 ml) that were subsequently flooded with nitrogen to avoid disulfide formation. After polymerization for 3 h at 37° C. gels had formed in all tubes containing cross-linker solution. To the gels 784 µl DTNB solution (50 mM sodium acetate, 2 mM 5,5'-Dithio-bis(2-nitrobenzoic acid) in $H_2O$) and 784 µl Tris (1 M Tris/pH 8.0) was added. Thereafter the hydrogels were crushed into small pieces and incubated while shaking at 200 rpm for 20 min. 100 µl from the supernatant was taken for the measurement and the absorption at 412 nm was measured with a plate reader. The percentage of reacted thiols was calculated as the absorption of the samples with different cross-linker concentrations divided by the absorption of the HA-SH solution without cross-linker.

Ellman's assay was used to quantify the efficiency of the cross-linking reaction between the acrylates in the linkers 5a and 5b and the thiols in HA-SH. The remaining free thiols were analyzed after 3 h of gelation in a range of 0 to 1.8 cross-linker equiv., defined as the number of acrylates divided by the number of thiols in the reaction. While below 0.8 equiv. the reaction efficiencies are close to 100%, higher cross-linker equiv. lead to slightly lower efficiencies, presumably due to steric hindrance. Furthermore, the reaction efficiency is not affected by the charge of the cross-linker as the data for both hydrogels show similar conversions.

Mechanical Characterization of the Hydrogels and Fitting Analysis

The mechanical properties of the HA-SH hydrogels were measured after equilibrium swelling was achieved on a MTS Nano Bionix Testing System using a parallel plate geometry in compression mode. Here the apparatus measures the force as a function of the applied strain. The analysis of the E-modulus was performed in the linear regime between 0 and 5% compression using a linear fit. In high compression mode each hydrogel was subjected to five subsequent strains of at least 60%. The hydrogel cylinders were not completely dried before the measurement to avoid barrel shape formation during compression. Drying-out of the hydrogels was not observed during the measurement. All measurements were carried out in triplicates.

The mechanical properties of HA-SH-5a and HA-SH-5b hydrogels with 1.0 cross-linker equiv. were first characterized in uniaxial compression tests for their behavior under high compression (FIG. 1A). FIG. 1A shows stress-strain curves for HA-SH-5a (black) and HA-SH-5b (white) hydrogels with 1.0 cross-linker equiv. $\sigma_n$ represents the nominal stress, $\lambda$ the deformation ratio. Solid black lines represent fitting curves based on equation (1), ($R^2$=0.9999 for both fittings).

The stress-strain data was recorded in the deformation range 0.55<$\lambda$<1, where $\lambda$ is the deformation ratio ($\lambda$=L/$L_0$, L and $L_0$ are the lengths of the deformed and undeformed samples). Measuring the nominal stress $\sigma_n$ (related to the undeformed cross-section of the gel), these tests showed that the hydrogels withstand repetitive compression (5 cycles) up to $\lambda$≈0.55 with no damage or alterations. Additionally both type of gels were found to show strain-stiffening behavior which is very accurately described by the formula $$\sigma_n = \frac{E}{3}\left(\lambda - \frac{1}{\lambda^2}\right)\exp\left(\frac{J_1}{J_m}\right); J_1 = \lambda^2 + \frac{2}{\lambda} - 3 \qquad (1)$$

where E represents the zero strain E-modulus and $J_m$ a strain invariant at which strain hardening becomes dominant, thereby accounting for a finite extensibility of the polymeric chains. Equation (1) derives from a strain energy density which was found to describe the elastic response of many biopolymer networks such as actin, collagen and vimentin.

From the fits for the HA-SH-5a and -b gels with 1.0 cross-linker equiv. (FIG. 1A), $J_m$=1.96 and $J_m$=2.10, respectively, was found. Taking the obtained values of $J_m$ and converting them to the maximum uniaxial extension ratio $\lambda_{max}$ yields 1.99 (1.96, 2.01) and 2.03 (1.83, 2.20), indicating that the polymeric chains in the network can be extended to about twice their original length before chains are strongly stiffening. Further, $J_m$ can be converted to a maximum compression ratio $\lambda_{max,c}$ which yields 0.42 (0.41, 0.43) and 0.41 (0.36, 0.47). The fact that the values of $\lambda_{max}$ are similar for both linkers indicated that the deformation of the hydrogels is mainly due to rearrangements of the polymeric backbones but not significantly influenced by the cross-linkers' charge.

Figure 1B:
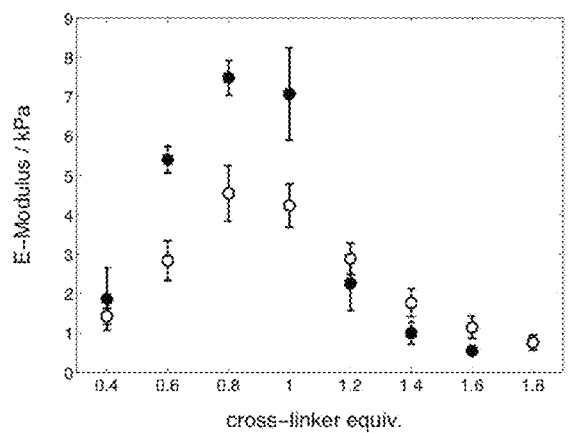

The zero strain E-moduli were also determined for different cross-linker equiv. values (FIG. 1B). FIG. 1B shows E-moduli of HA-SH-5a (black) and HA-SH-5b (white) hydrogels measured by uniaxial compression testing between parallel plates. All experiments were performed in triplicates. Error bars represent SEM.

Gels formed with cross-linker equiv. between 0.8 and 1.0 show the highest elastic moduli. At 1.0 cross-linker equiv. E=7.1±1.2 kPa for HA-SH-5a and E=4.2±0.5 kPa for HA-SH-5b. Hydrogels formed with both higher and lower cross-linker equiv. resulted in softer gels with lower E-moduli: The increase of the elastic moduli up to 0.8 equiv. correlates with the increasing number of thiols reacting with the cross-linker up to this point.

At higher equivalents an increasing number of cross-linkers are more likely to attach only with one arm to the hyaluronan backbone and therefore the mechanical stability decreases in both type of hydrogels. The hydrogels with 1.0 cross-linker equiv. show good long term stability as their E-moduli remained unchanged even after 1 week of incubation at 37° C. in PBS which makes them suitable for cell culture applications.

TABLE 1

Long-term stability of HA-SH-5a and HA-SH-5b hydrogels. HA-SH (58% thiolated) hydrogels were produced with 1.0 equiv. cross-linker, stored in PBS at 37° C. and the E-moduli were measured over time. The hydrogels are stable over a week and showed no sign of degradation.

|  | after swelling | 2 days | 1 week |
| --- | --- | --- | --- |
| HA-SH-5a | 100 ± 7.65 | 107.23 ± 7.57 | 100.34 ± 8.92 |
| HA-SH-5b | 100 ± 20.72 | 90.87 ± 13.36 | 87.56 ± 3.46 |

The charge of the cross-linker also has a clear effect on the elastic moduli of the hydrogels. In the regime of up to 1.0 cross-linker equiv., hydrogels with the positively charged cross-linker 5b show lower E-moduli than the hydrogels with the neutral cross-linker 5a. At higher cross-linker equivalents, this trend is reversed (FIG. 1B). Above a critical ratio corresponding to 1.6 equiv. for 5a and 1.8 for 5b no form-stable cylindrical gels could be created.

Measurement of Hydrogel Swelling Ratios

The swelling ratio of the hydrogels was taken as the wet weight of the hydrogels after swelling to equilibrium in PBS divided by the dry weight of the hydrogels which was calculated from the polymer and cross-linker concentration used and the volume of the cylindrical wells.

Figure 1C:
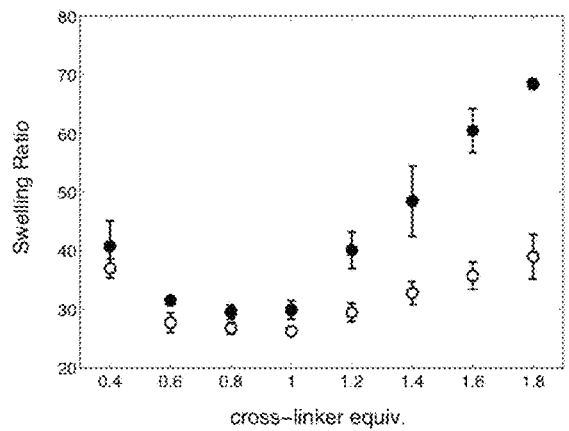
Figure 2A:
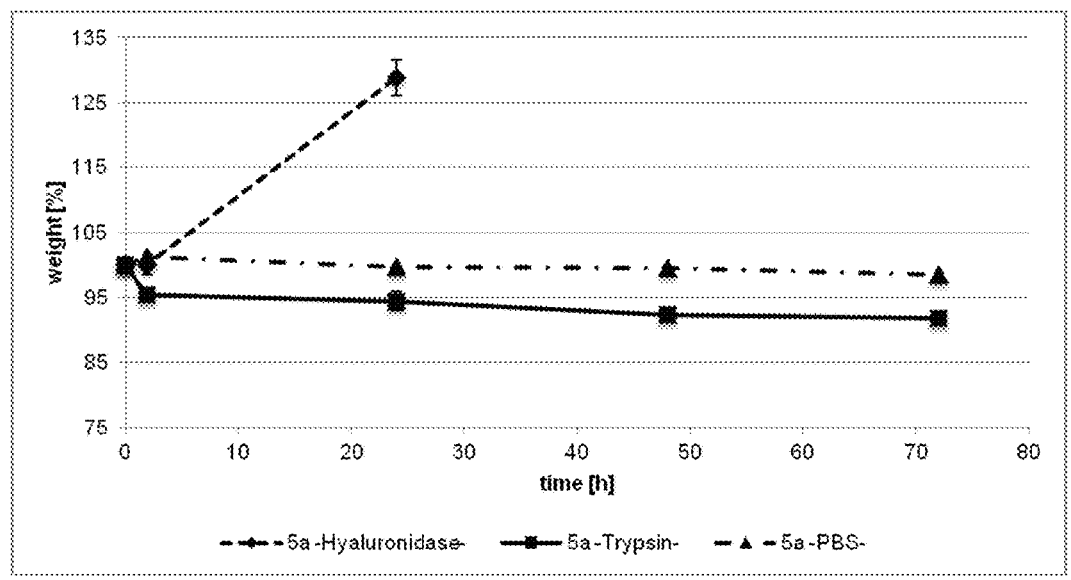
FIGS. 2A and 2B show the stability of HA-SH hydrogels with 49% thiol groups against 2 enzymes (hyaluronidase and trypsin) and PBS.
Figure 2B:
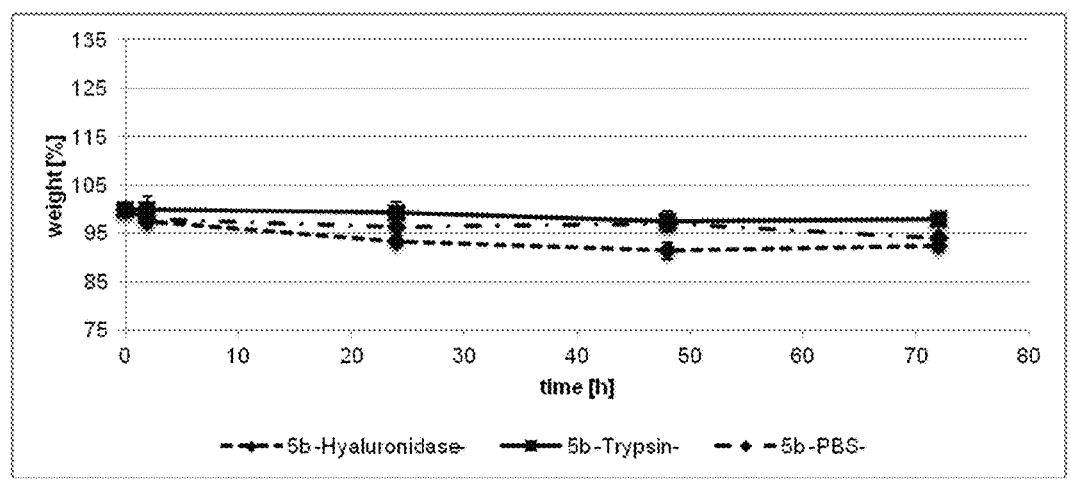
Figure 3A:
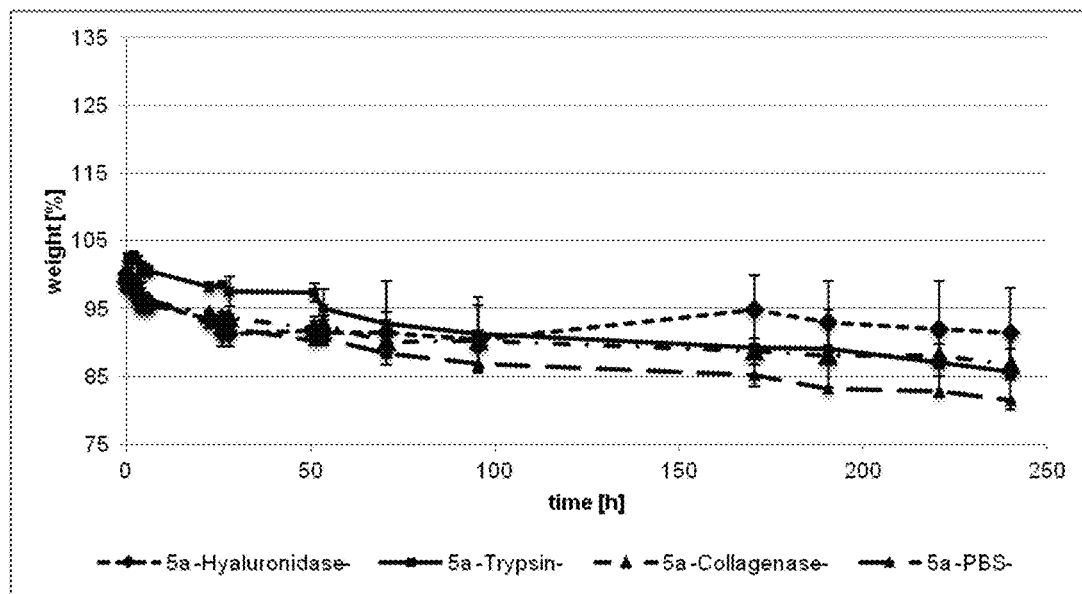
FIGS. 3A and 3B shows the stability of HA-SH hydrogels with 58% thiol groups against 2 enzymes (hyaluronidase and trypsin) and PBS.
Figure 3B:
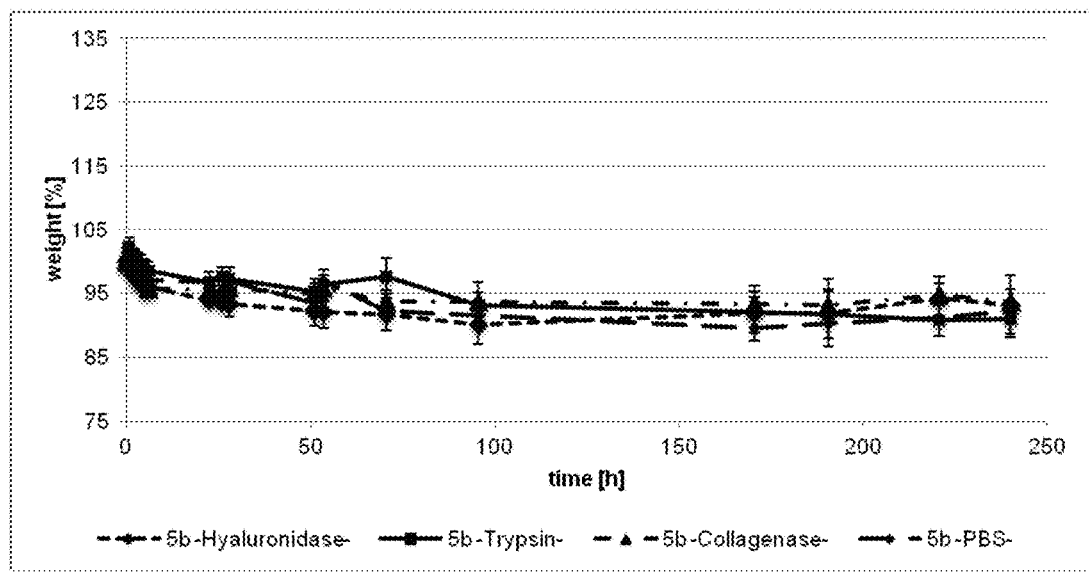
Figure 4A:
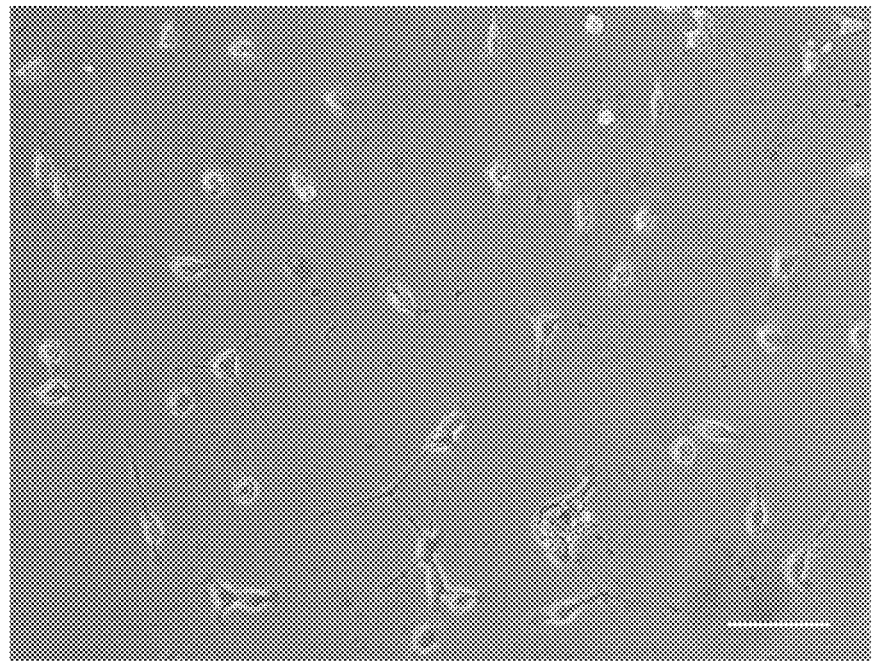
FIGS. 4A, B, C and D show the adhesion and proliferation of REF 52 wt cells on HA-SH hydrogels with 58% thiol groups
Figure 4B:
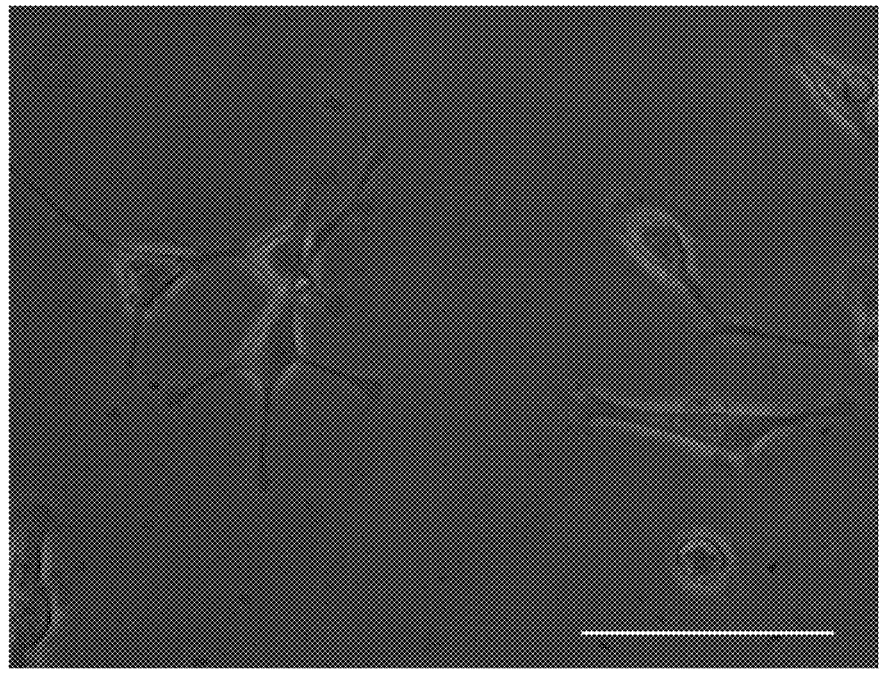
FIG. 4B: cross-linker 5a; 1 week later
Figure 4C:
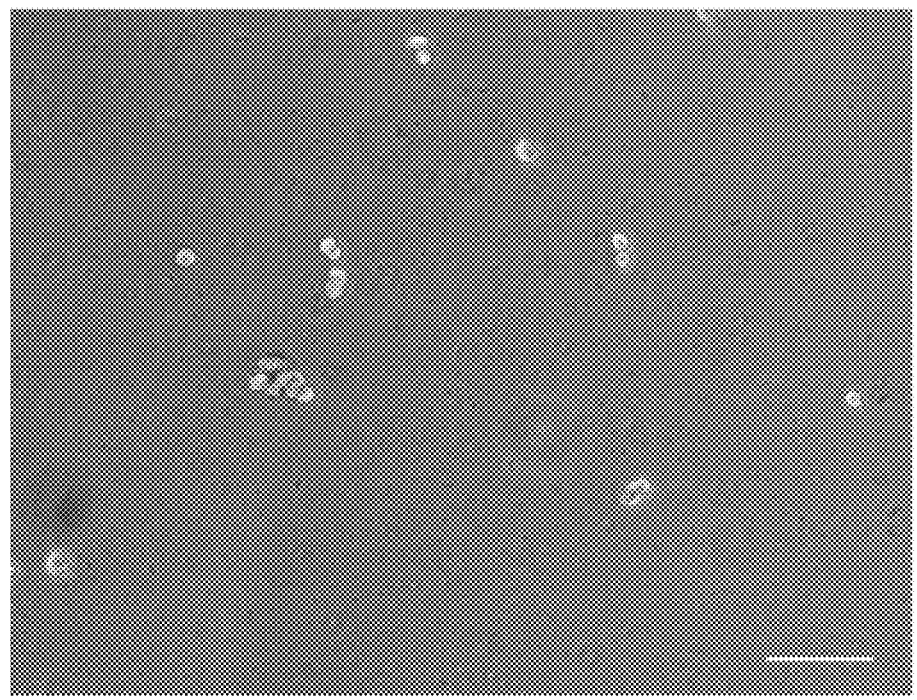
FIG. 4C: cross-linker 5b; after seeding
Figure 4D:
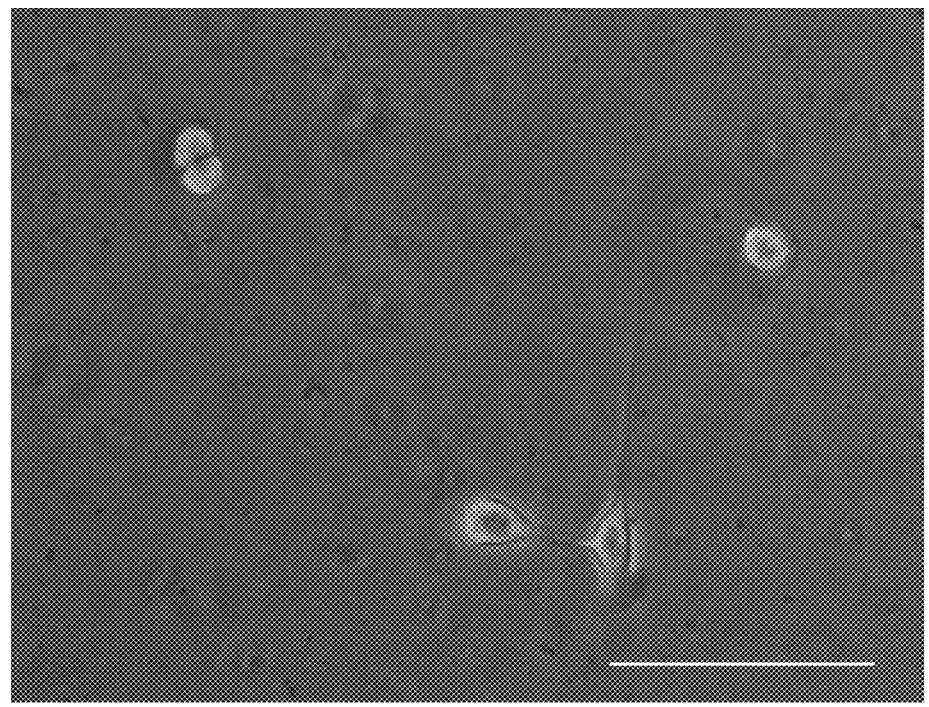
FIG. 4D: cross-linker 5b; 1 week later The present invention is further illustrated by the following non-limiting examples.

In the regime where the E-moduli show a maximum (between 0.8 and 1.0 equiv., compare FIG. 1B), the swelling ratio shows a minimum (FIG. 1C).

FIG. 1C shows the swelling ratio of HA-SH-5a (black) and HA-SH-5b (white) hydrogels. All experiments were performed in triplicates. Error bars represent SEM.

At low cross-linker equiv. hydrogels formed with the two different cross-linkers show similar swelling ratios). At higher cross-linker equivalents, however, the hydrogels with positively charged cross-linker 5b show lower swelling ratios compared to hydrogels with 5a.

The swelling ratio of HA-SH-5a hydrogels goes up to ≈60 whereas the swelling ratio of HA-SH-5b hydrogels only reaches ≈35 at 1.6 cross-linker equiv. This shows that the positive charge on the linker interacts with the negatively charged hyaluronan backbone and may play an important role in the secondary structure of the gel.

Isolation and Cell Culture of Primary Human Fibroblasts

Primary human fibroblasts were isolated according to Kluger et al. (*J Mater Sci Mater Med.* 2010, 21, 2665-2671) and seeded at a density of $0.6 \times 10^4$ cells $cm^{-2}$ in tissue culture flasks. After 72 h incubation time at 37° C. in a 5% $CO_2$ humidified atmosphere, non-adherent cells were removed and adherent cells were expanded for further experiments.

In Vitro Cytotoxicity Testing of Material According to DIN ISO 10993-5 Via Extraction The in vitro biocompatibility of the hydrogels was tested referring to DIN ISO 10993-12: 2009 on a sub confluent monolayer culture of human fibroblasts. Therefore, materials were extracted in DMEM for 72 h. All tests were performed in 96-well tissue culture plates. One day after the inoculation of $2 \times 10^4$ fibroblasts per well, the extracts were supplemented with 10% FCS and were added to the cells. After further 24±2 hours at 37° C. and 5% $CO_2$, cell growth was determined by a cell proliferation assay WST-1 (Roche Diagnostic GmbH, Mannheim, Germany). A 10% WST-1 solution in PBS was prepared and incubated for 30 minutes at 37° C. and 5% $CO_2$. The absorbance was determined at 492 nm using an ELISA reader. The absorbance was calculated as percentage of the proliferation with respect to the positive control (DMEM with 10% FCS) and negative control (DMEM with 10% FCS supplemented with 0.1% SDS).

Hydrogels cross-linked by 5b showed a weak cytotoxicity whereas the 5a linked hydrogels are non-cytotoxic. No significant differences between the hydrogel interconnectivity were detected (n=3).

Summarizing, these semi-synthetic hydrogels were stable when stored in PBS buffer at 37° C. and do not decompose due to ester cleavage in the cross-linker. The cross-linking density was found to be the main determinant of the gel stiffness, which allows tuning of the gel properties in a range important for the engineering of soft tissues. The stiffest gels were obtained at ca. 0.8 crosslinker equiv. and the E-Moduli were similar to those found for human skin. Gel properties such as the swelling ratio and the E-moduli were significantly influenced by the charge on the cross-linker due to ionic interactions with the polymer backbones. Thus the charge on the cross-linker has an important effect on hyaluronan hydrogels, an observation which has not been previously reported.

The invention claimed is:

1. A cross-linked hydrogel, comprising:
   a thiolated or aminated biopolymer selected from the group consisting of a polysaccharide and a polyaminosaccharide; and
   at least one bifunctional pyridine-based cross-linker selected from 3a, 4a, 5a, 3b, 4b and 5b:

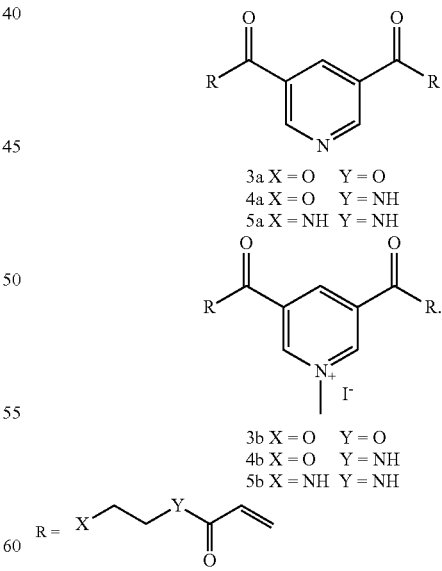

2. The cross-linked hydrogen according to claim 1, wherein the biopolymer is a thiolated hyaluronic acid.

3. The cross-linked hydrogel according to claim 1 which comprises a combination of at least 2 different bifunctional pyridine-based cross-linkers.

4. The cross-linked hydrogel according to claim 2 which is resistant to degradation by hyaluronidases.

5. The cross-linked hydrogel according to claim 1, wherein a charge of the at least one bifunctional pyridine-based cross-linker is adjustable in response to a pH of the cross-linked hydrogel's surrounding.

6. The cross-linked hydrogel according to claim 1, further comprising nanoparticles covalently bound thereto.

7. A material composition comprising a cross-linked hydrogel comprising:
   a thiolated or aminated biopolymer selected from the group consisting of a polysaccharide and a polyaminosaccharide; and
   at least one bifunctional pyridine-based cross-linker selected from 3a, 4a, 5a, 3b, 4b and 5b:

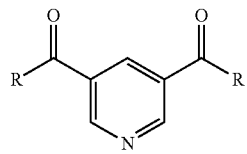

3a X = O    Y = O
4a X = O    Y = NH
5a X = NH   Y = NH

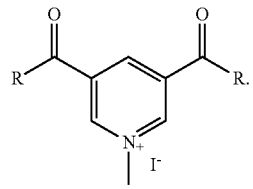

3b X = O    Y = O
4b X = O    Y = NH
5b X = NH   Y = NH

8. The cross-hydrogel according to claim 1, wherein the at least one bifunctional pyridine-based crosslinker is 5a or 5b.

9. The cross-linked hydrogel according to claim 1, wherein the biopolymer is selected from the group consisting of cellulose, chitin, chitosan, chondroitinsulfate, dextran, hyaluronic acid and block-copolymers thereof.

* * * * *